US008496969B2

(12) United States Patent
Wynn et al.

(10) Patent No.: US 8,496,969 B2
(45) Date of Patent: Jul. 30, 2013

(54) SOFT TABLET CONTAINING HIGH MOLECULAR WEIGHT CELLULOSICS

(75) Inventors: David Wynn, Abington, PA (US); Nick Parikh, Long Valley, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 394 days.

(21) Appl. No.: 12/638,070

(22) Filed: Dec. 15, 2009

(65) Prior Publication Data

US 2010/0092555 A1 Apr. 15, 2010

Related U.S. Application Data

(63) Continuation of application No. 10/607,766, filed on Jun. 27, 2003, now abandoned.

(51) Int. Cl.
*A61K 9/50* (2006.01)

(52) U.S. Cl.
USPC ........... 424/502; 424/439; 424/441; 424/489; 424/490; 424/493; 424/494; 424/499

(58) Field of Classification Search
None
See application file for complete search history.

(56) References Cited

U.S. PATENT DOCUMENTS

| | | | |
|---|---|---|---|
| 4,818,539 A | 4/1989 | Shaw et al. | |
| 4,835,187 A | 5/1989 | Reuter et al. | |
| 4,851,226 A | 7/1989 | Julian et al. | |
| 4,851,232 A | 7/1989 | Urquhart et al. | |
| 4,882,154 A | 11/1989 | Yang et al. | |
| 4,906,478 A | 3/1990 | Valentine et al. | |
| 5,075,114 A | 12/1991 | Roche | |
| 5,275,822 A | 1/1994 | Valentine et al. | |
| 5,336,486 A | 8/1994 | Acharya | |
| 5,441,933 A * | 8/1995 | Lattanzi et al. | 514/11.9 |
| 5,489,436 A | 2/1996 | Hoy et al. | |
| 5,532,244 A | 7/1996 | Wong et al. | |
| 5,637,313 A | 6/1997 | Chau et al. | |
| 5,789,393 A | 8/1998 | Dressman et al. | |
| 5,876,759 A | 3/1999 | Gowan, Jr. | |
| 5,989,534 A | 11/1999 | Samain | |
| 6,103,260 A | 8/2000 | Luber et al. | |
| 6,117,451 A * | 9/2000 | Kumar | 424/465 |
| 6,432,442 B1 | 8/2002 | Buehler et al. | |
| 6,451,345 B1 | 9/2002 | Percel et al. | |
| 6,471,991 B2 | 10/2002 | Robinson et al. | |
| 6,576,260 B2 | 6/2003 | Ziegler et al. | |
| 2002/0031552 A1 | 3/2002 | McTeigue et al. | |
| 2002/0122823 A1 | 9/2002 | Bunick et al. | |
| 2004/0265373 A1 | 12/2004 | Wynn et al. | |
| 2007/0207214 A1 | 9/2007 | Castan et al. | |
| 2009/0104267 A1 | 4/2009 | Wynn et al. | |

FOREIGN PATENT DOCUMENTS

| | | |
|---|---|---|
| JP | P200-95710 | 4/1990 |
| JP | 5306229 | 11/1993 |
| WO | WO 95/02391 | 1/1995 |
| WO | WO 96/15775 | 5/1996 |
| WO | WO 88/06893 | 9/1998 |
| WO | WO 00/09090 | 2/2000 |
| WO | WO 00/30617 | 6/2000 |
| WO | WO 01/52848 | 7/2001 |
| WO | WO 02/03964 | 1/2002 |

OTHER PUBLICATIONS

"Thermal and Rheolgocial Evaluation of Pharmaceutical Excipients for Hot Melt Extrusion" Dow Chemical Co. Poster presented at the annual meeting and exposition of the American Association of Pharmaceutical Scientists, Nov. 7-9, 2004.*
USP 23, (1995) <1216> p. 1981.
USP 24, 2000 Version, 19-20 and 856-857 (1999).
Lieberman, et al., Pharmaceutical Dosage Forms, vol. 3, pp. 138-150 (1990).
Lachman et al., The Theory and Practice of Industrial Pharmacy, Chapter 11, pp. 293-345 ($3^{rd}$ Ed. 1986).
Lieberman et al., Pharmaceutical Dosage Forms—Tablets, vol. 2, $2^{nd}$ ed., Marcel Dekker Inc., 1990, pp. 213-217, 327-329.
"Thermal and Rheological Evaluation of Pharmaceutical Excipients for Hot Melt Extrusion" Dow Chemical Co. Poster presented at the annual meeting and exposition of the American Association of Pharmaceutical Scientists, Nov. 7-9, 2004.
Lachman et al., The Theory and Practice of Industrial Pharmacy, Lea & Febiger Publishing, pp. 315-317.
http://www.dow.com/dowexcipients/products/methocel.htm.
http://www.colorcon.com/pharma/mod_rel/methocel/literature/methocel_e4m.pdf.
http://www.colorcon.com/pharma/mod_rel/methocel/literature/methocel_k4m.pdf.
EP Search Report for Appl. No. 04253843.9 dated Sep. 19, 2004.
EP Search Report for Appl. No. 04253844.7 dated Sep. 19, 2004.

* cited by examiner

*Primary Examiner* — James Rogers

(57) ABSTRACT

The invention relates to an immediate release tablet capable of being chewed or disintegrated in the oral cavity, which comprises a pharmaceutically active ingredient having an optional tastemasking coating, and a matrix comprising hydroxyalkylcellulose having a weight average molecular weight of from about 60,000 to about 5,000,000. The tablet possesses exceptionally good mouthfeel and stability.

20 Claims, No Drawings

SOFT TABLET CONTAINING HIGH MOLECULAR WEIGHT CELLULOSICS

CROSS REFERENCE TO RELATED APPLICATIONS

This is a continuation of prior U.S. Application U.S. Ser. No. 10/607,766, filed Jun. 27, 2003 now abandoned, which is incorporated by reference herein in its entirety.

BACKGROUND OF THE INVENTION

1. Field of the Invention

The present invention relates to an immediate release, chewable or disintegrable tablet comprising a blend of active ingredient and high molecular weight cellulosics, having exceptionally good mouthfeel and stability.

2. Background of the Invention

Pharmaceuticals intended for oral administration are typically provided in solid dosage forms such as, for example, tablets, capsules, pills, lozenges, or granules. Tablets are swallowed whole, chewed in the mouth, or dissolved in the oral cavity. Chewable or disintegrable tablets are often employed in the administration of pharmaceuticals where it is impractical to provide a tablet for swallowing whole, such as, for example, with pediatric and geriatric patients.

Workers in the field continue to try to improve the flavor and mouthfeel of chewable tablets and other comestibles by adding agents, such as gums, thereto. See, e.g., U.S. Pat. No. 4,818,539 and WO 88/06893. In order to effectively texture mask such dosage forms, it is necessary to blend a high level of gum with the active agent. Disadvantageously, during mastication such forms become pasty and initially cause a significant drying phase in the mouth.

Alternative texture masking agents include polyalkylene glycols. For instance, U.S. Pat. No. 4,882,154 discloses chewable dosage forms wherein the pharmaceutical ingredient is pre-coated with, for example, a polyalkylene glycol having a molecular weight of less than 3700. Further, WO 00/30617 discloses a taste masked drug particle having an active inner core, a polyethylene oxide layer covering the core, and an outer taste masking layer. However, these texture masking processes disadvantageously require one or more coating steps, which not only makes them less economical but also increases production cycle time.

Another technique for texture masking an agent involves the blending of low-viscosity hydroxyalkylcellulose and high-viscosity hydroxyalkylcellulose with calcium powder, then granulating the blend into pelletizable granules in order to improve the mouth feel of the resulting calcium-containing dosage forms. See, e.g., Japanese Patent Application 5[1993]-306229.

U.S. Pat. No. 6,432,442 discloses the use of a gelatin matrix and an optional hydrocolloid as another technique for providing a soft, chewable delivery system. Because these "gummi" or confectionary systems also contain water in an amount of from about 10 to 30 percent by weight of the final product, they disadvantageously possess certain limitations with respect to shelf-life, packaging, and storage conditions. Additionally, it is economically more beneficial to produce other dosage forms such as, for example, compressed tablets, due to their simplicity of processing.

It would be desirable to have a chewable or disintegrable, texture masked, immediate release dosage form, and in particular a chewable or disintegrable compressed tablet, that could be suitable for use with active agents having large particle sizes, e.g. those in excess of 100 microns.

SUMMARY OF THE INVENTION

This invention relates to an immediate release dosage form capable of being chewed or disintegrated in the oral cavity prior to swallowing, comprising, consisting of, and/or consisting essentially of
  a. a plurality of particles comprising a pharmaceutically active ingredient, said particles having a particle size of about 150 μm to about 400 μm; and
  b. a matrix comprising, based upon the total weight of the dosage form, from about 0.1 percent to about 25 percent of hydroxyalkylcellulose having a weight average molecular weight of from about 60,000 to about 5,000,000 and/or a viscosity of from about 3,000 mPa·S to about 150,000 mPa·s in a 2% aqueous solution.

This invention further relates to an immediate release dosage form capable of being chewed or disintegrated in the oral cavity prior to swallowing, comprising, consisting of, and/or consisting essentially of
  a. a plurality of particles comprising a pharmaceutically active ingredient; and
  b. a matrix comprising, based upon the total weight of the dosage form, from about 0.1 percent to about 25 percent of hydroxyalkylcellulose having a weight average molecular weight of from about 60,000 to about 5,000,000 and/or a viscosity of from about 3,000 mPa·S to about 150,000 mPa·s in a 2% aqueous solution,
wherein the pharmaceutically active ingredient is coated with a taste masking coating.

DETAILED DESCRIPTION OF THE INVENTION

As used herein, the term "dosage form" applies to any solid, semi-solid, or liquid composition designed to contain a specific pre-determined amount or "dose" of a certain ingredient, for example an active ingredient as defined below. Dosage forms may include, but are not limited to: a) pharmaceutical drug delivery systems, including those for oral administration, buccal administration, or mucosal delivery; or b) compositions for delivering minerals, vitamins and other nutraceuticals, oral care agents, flavorants, and the like. In one embodiment, the solid dosage form is an orally administered system for delivering a pharmaceutical active ingredient to the GI tract of a mammal. The dosage forms of the present invention are typically considered to be solid; however, they may contain liquid or semi-solid components. Suitable "solid dosage forms" of the present invention include, but are not limited to, tablets, e.g. caplets; capsules; sachets; and the like. One suitable solid dosage form is a chewable or orally disintegratable tablet.

As used herein, the term "immediate release" shall mean that the dissolution of the dosage form conforms to USP specifications for immediate release tablets containing the particular active ingredient employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). The term, "good mouth feel"

shall mean that the dosage form becomes a slippery, gel-like mass capable of suspending gritty particles during mastication.

By "high weight average molecular weight hydroxyalkylcellulose," it is meant a hydroxyalkylcellulose having a) weight average molecular weight between about 60,000 to about 5,000,000, e.g. from about 140,000 to about 1,150,000; and/or b) a viscosity between about 3,000 mPa·s to about 150,000 mPa·s in a 2% aqueous solution, e.g., from about 4,000 mPa·s to about 100,000 mPa·s in a 2% aqueous solution.

The dosage form of the present invention may be made from a composition comprising one or more active ingredients and, based upon the total weight of the dosage form, from about 0.1 percent to about 25.0 percent, e.g. from about 0.5 percent to about 10.0 percent, of a hydroxyalkylcellulose having a high weight average molecular weight in the matrix.

The phrase "hydroxyalkylcellulose having a high weight average molecular weight in the matrix," as used herein, shall refer to such a hydroxyalkylcellulose that is present in the final dosage form but is not contained in the active ingredient powder or the granulated active ingredient particles or crystals per se. In one embodiment, the granulated active ingredient particles are substantially free of high weight average molecular weight hydroxyalkylcellulose. As used herein, "substantially free of high weight average molecular weight hydroxyalkylcellulose" shall mean that the granulated particles contain, based upon the total weight of the particles, less than about 1%, e.g., less than about 0.1% or less than about 0.01% of high weight average molecular weight hydroxyalkylcellulose.

Suitable active ingredients include pharmaceuticals, minerals, vitamins, other nutraceuticals, and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep aids, urinary tract agents and mixtures thereof.

Examples of suitable gastrointestinal agents include stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine; proton pump inhibitors; gastrointestinal cytoprotectives, such as sucraflate and misoprostol; gastrointestinal prokinetics, such as Prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment, the active agent may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active agent may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment, the active agent may be selected from pseudoephedrine, phenylpropanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient(s) are present in the dosage form in a therapeutically effective amount, which is an amount that produces the desired therapeutic response upon oral administration and can be readily determined by one skilled in the art. In determining such amounts, it is well known in the art that various factors must be considered that include, but are not limited to the particular active ingredient being administered, the bioavailability characteristics of the active ingredient, the dose regime, and the age and weight of the patient.

In one embodiment, the amount of active ingredient contained in the dosage form is, based upon the total weight of the dosage form, from about 0.25 percent to about 70 percent, e.g., from about 0.5 percent to about 25 percent or from about 10 percent to about 50 percent.

The active ingredient can be in the form of a fine powder, granule, or large crystal, and typically has an average particle size from about 20 microns to about 1000 microns, e.g., from about 50 microns to about 700 microns or from about 100 microns to about 500 microns. In one embodiment, one or more active ingredients are contained in particles having an average size from about 150 to about 400 microns. The active ingredient may be in any form within the particles, for example as a fine powder dispersed throughout a matrix of inactive ingredients, or in crystalline or amorphous form, layered onto an inert seed particle.

If the active ingredient has an objectionable taste, a coated particle containing the active ingredient coated with a taste masking agent is employed. "Coated particle," as used herein, refers to a solid active ingredient in the form of a crystal or particle, an agglomerate of individual particles, or a granuled particle, which has been encapsulated with a taste masking agent, either by film coating method known in the art or by other known processes such as coaccervation. For example, acetaminophen particles that have been encapsulated with ethylcellulose or other polymers via coaccervation may be used in the present invention. Such coaccervation-encapsulated acetaminophen may be purchased commercially from Eurand America, Inc. Vandalia, Ohio, or from Circa Inc., Dayton, Ohio. Other commercially available taste masked active ingredients may also be employed.

Suitable taste masking coatings are described in, for example, U.S. Pat. Nos. 6,471,991, 4,851,226, 5,075,114, and 5,489,436, which are all incorporated by reference herein.

Examples of suitable taste masking agents include, but are not limited to cellulose acetate, ethylcellulose, poly(ethyl acrylate, methyl methacrylate, trimethylammonioethyl methacrylate chloride), which is commercially available from Rohm Pharma under the tradename, "EUDRAGIT", hydroxypropyl methylcellulose, hydroxypropyl cellulose, hydroxyethyl cellulose, and mixtures thereof.

In certain embodiments, the taste masking agent may be comprised of a mixture of a) at least one solubilizable polymer selected from the group consisting of enteric polymers, reverse enteric polymers, water soluble polymers, and copolymers and mixtures thereof; and b) and at least one insoluble film forming polymer. "Solubilizable polymer" as used herein, shall mean a polymer that swells or dissolves in a certain medium and can be dispersed at the molecular level to form a homogeneous dispersion therein. The medium may resemble conditions that could exist in the gastrointestinal tract of a human. For example, the solubilizable polymer may be soluble in a water medium (e.g. water soluble polymers). Alternatively the solubilizable polymer may be soluble in an aqueous medium having a certain pH range, such as at a pH less than 5 (e.g. reverse enteric polymers) or such as at a pH of 5.5 or greater (e.g. enteric polymers).

The enteric polymer may be selected from any one of a variety of known enteric polymers, such as shellac, hydroxypropyl methylcellulose phthalate, hydroxypropyl methylcellulose acetate succinate, cellulose acetate phthalate, polyvinylacetate phthalate, and polymethacrylate-based polymers such as poly(methacrylic acid, methyl methacrylate) 1:2, which is commercially available from Rohm Pharma GmbH under the tradename, "EUDRAGIT S" polymers, and poly(methacrylic acid, methyl methacrylate) 1:1, which is commercially available from Rohm Pharma GmbH under the tradename, "EUDRAGIT L" polymers. Combinations of enteric polymers may also be used.

In one embodiment, the enteric polymer is selected from non-acrylate compounds, specifically hydroxypropyl methylcellulose phthalate, hydroxypropyl methylcellulose acetate succinate, cellulose acetate phthalate, and polyvinylacetate phthalate. Non-acrylates are preferred because acrylate polymers tend to become tacky and agglomerate at high temperature. Cellulose polymers are more heat stable than acrylate polymers. In addition, acrylate polymers are known to have a characteristic, slightly unpleasant taste, whereas cellulose polymers have a more neutral taste profile.

Examples of suitable reverse enteric polymers include, but are not limited to methylaminoethyl-methacrylate and neutral methacrylic acid esters available from Rohm Pharma GmbH, Germany under the tradename, "EUDRAGIT™ E 100."

Examples of suitable water soluble polymers include, but are not limited to hydroxypropylmethylcellulose, hydroxypropylcellulose, hydroxyethylcellulose, methylcellulose, polyvinyl pyrrolidone, polyethylene glycol, polyvinyl alcohols, and sodium carboxymethylcellulose.

The insoluble film forming polymer may be selected from a number of known compounds, including cellulose acetate, cellulose acetate butyrate, cellulose triacetate, ethylcellulose, neutral ester co-polymer of ethyl acylate and methyl methacrylate, which is commercially available from Rohm Pharma under the tradename, "EUDRAGIT NE", and poly (ethyl acrylate, methyl methacrylate, trimethylammonioethyl methacrylate chloride) 1:2:0.1, which is commercially available from Rohm Pharma under the tradename, "EUDRAGIT RS". One or more than one insoluble film forming polymer may be used. Preferably, the insoluble film forming polymer is impermeable and does not swell in an aqueous environment. More preferably, the insoluble film forming polymer is selected from cellulose acetate and ethylcellulose.

The weight ratio of solubilizable polymer to insoluble film forming polymer in the polymeric coating is preferably in the range of about 5:95 to about 80:20, more preferably about 40:60 to about 70:30.

Other examples of suitable taste masking coatings are provided in the following table:

| POLYMER SYSTEM | COAT LEVEL[1] | POLYMER RATIO[2] |
|---|---|---|
| Cellulose acetate/PVP | 5-60% | 90/10 to 60/40 |
| Cellulose acetate Butyrate/PVP | 5-60% | 90/10 to 60/40 |
| Cellulose acetate/HPC | 5-60% | 90/10 to 50/50 |
| Cellulose acetate/HPMCP | 5-60% | 90/10 to 50/50 |
| Cellulose acetate Butryate/HPC | 5-60% | 90/10 to 50/50 |
| Cellulose acetate/EUDRAGIT E100 | 8-60% | ALL RATIOS |
| Cellulose acetate Butryate/EUDRAGIT E 100 | 8-60% | ALL RATIOS |
| Ethyl cellulose/PVP | 8-60% | 90/10 to 60/40 |
| Ethyl cellulose/HPC | 8-60% | 90/10 to 50/50 |
| Ethyl cellulose/EUDRAGIT E 100 | 8-60% | ALL RATIOS |
| HPC | 10-60% | NA |
| HEC | 10-60% | NA |
| EUDRAGIT E 100 | 10-60% | NA |
| HPMC | 10-60% | NA |
| HEC/HPMC | 10-60% | ALL RATIOS |
| HPC/HPMC | 10-60% | ALL RATIOS |
| HEC/HPC | 10-60% | ALL RATIOS |
| 2-vinyl pyridine styrene co-polymer | 10-60% | NA |
| CA/2-vps | 8-60% | ALL RATIOS |
| CAB/2-vps | 8-60% | ALL RATIOS |
| Ethyl cellulose/2-vps | 8-60% | ALL RATIOS |
| Cellulose triacetate/PVP | 8-60% | 90/10 to 60/40 |
| Cellulose triacetate/HPC | 8-60% | 90/10 to 50/50 |
| Cellulose triacetate/EUDRAGIT E 100 | 8-60% | ALL RATIOS |

[1]percent by weight of the coated particle in a dried state
[2]by weight
PVP = polyvinylpyrrolidone
HPC—hydroxypropyl cellulose
HEC—hydroxylethyl cellulose
HPMC—hydroxypropylmethyl cellulose
CA—cellulose acetate
CAB—cellulose acetate butyrate
2-vps—2 vinyl pyridine styrene
HPMCP—hypromellose pthalate (also known as hydroxypropylmethyl cellulose)
EUDRAGIT ™ E 100—methylaminoethyl- methacrylate and neutral methacrylic acid esters available from Rohm Pharma GmbH, Germany.

The taste masking polymers may also optionally be combined with a surfactant. Suitable surfactants include both ionic and non-ionic materials from both synthetic and natural origins, including but not limited to lecithin, glyceryl esters, sugar esters, polysorbates, mono and diglycerides of fatty acids, propylene glycol esters, sucrose fatty acid esters, polyoxyethylene derivatives of sorbitan fatty acid esters, and mixtures thereof. Examples of useful polysorbates include sorbitan trioleate, sorbitan monopalmitate, sorbitan monolaurate, propylene glycol monolaurate, glycerol monostearate, diglycerol monostearate, glycerol lactyl-palmitate. Lactic acid derivatives include sodium stearoyl lactylate and calcium stearoyl lactylate. When a surfactant is present in the taste masking coating, the level of surfactant is present in an amount, based upon the total weight of the taste masking coating layer, from about 2% to about 10%.

In one embodiment, the dried taste masking coating comprises about 53 wt % hydroxypropyl methylcellulose phthalate ("hypromellose phthalate"), about 43 wt % cellulose acetate, and about 4 wt % polysorbate.

The taste masking coating may be coated directly onto the pure active ingredient core or may be coated on to a granulated particle core containing the active ingredient, such that the core is substantially covered. As used herein, "substantially covered" shall mean at least about 95%, e.g. about 99% of the exterior surface of the core is covered with the subject coating.

The taste masking coating is preferably applied to the active ingredient, or a granulated particle containing the active ingredient, in the form of a solution using conventional fluidized bed technology, such as Wurster coating or rotor coating. These coating operations are further described in Leiberman, et al., 3 *Pharmaceutical Dosage Forms* 138-150 (1990), which is hereby incorporated by reference.

A wide variety of organic solvents may be used to prepare the solution of the taste masking coating. Useful solvents include any of the pharmaceutically suitable organic solvents such as acetone, methanol, ethanol, isopropanol; aqueous solvents such as water; and mixtures thereof. Generally, the proportion of the taste masking coating in the solvent solution will be within the range of about 5 to about 20, e.g. from about 8 to about 15, weight percent, depending on the solvent and other similar considerations. One suitable solvent mixture includes acetone and water at a ratio from about 85:15 to about 95:5.

When a fluidized bed coating operation is used, air, which may be heated, passes through a bed of the active ingredient solids to fluidize them, and the solution of the taste masking composition is sprayed onto the fluidized bed and thereby coats the active. The air passing through the bed dried the coating onto the active ingredient, so that a dry coated granule is obtained.

The thickness of the taste masking coating on the active ingredient-containing core is typically from about 1 micron to about 20 microns, e.g. from about 2 microns to about 15 microns or from about 4 to about 9 microns.

Particles coated with a taste masking coating, in a dried state, generally contain the taste masking coating in an amount, based upon the total weight of particle and the taste masking coating, from about 1 percent to about 50 percent, e.g. from about 15 percent to about 25 percent. The exact proportions of the coating to the active ingredient can vary depending upon, for example, the level of tastemasking required and whether a sustained or immediate release of the active ingredient is desired. Increased amounts of the taste masking coating tend to provide a sustained release effect and enhanced taste masking.

In embodiments employing a granulated particle, such as a rotogranulated particle, the active ingredient will constitute from about 5 to about 90 weight percent of the particle, with the remainder being the binder or filler. Suitable binders for the granulated particles include polyvinyl pyrrolidone, hydroxypropylmethyl cellulose, hydroxypropyl cellulose, and other pharmaceutically acceptable polymers. Fillers suitable for use in such granulated particles include lactose, confectioner's sugar, mannitol, dextrose, fructose, other pharmaceutically acceptable saccharide and microcrystalline cellulose.

According to the dosage form of the present invention, the active ingredient may be combined with a matrix comprising a high weight average molecular weight hydroxyalkylcellulose, wherein the high weight average molecular weight hydroxyalkylcellulose is present in the matrix in an amount, based upon the total weight of the dosage form, from about 0.1 percent to about 25 percent, e.g. from about 0.5 percent to about 10 percent. The average particle size of the high weight average molecular weight hydroxyalkylcellulose may vary from about 1 micron to about 500 microns, e.g., from about 150 microns to about 400 microns or from about 200 microns to about 300 microns.

For optimal dissolution results, it is preferable to employ such hydroxyalkylcelluloses that have average molecular weights in the lower end of the range of "high weight average molecular weight" hydroxyalkylcelluloses as defined herein, as well as to employ the lowest level of such hydroxyalkylcelluloses that may yield the desired mouthfeel for the selected active ingredient.

"Hydroxyalkylcellulose," as used herein shall mean cellulose derivatives that are substituted with a hydroxyalkyl group, wherein the alkyl group contains from about 1 to about 10 carbons. Examples of suitable high molecular weight hydroxyalkylcelluloses include, but are not limited to, hydroxymethylcellulose, hydroxyethylcellulose, hydroxypropylcellulose, hydroxyethylmethylcellulose, hydroxypropylmethylcellulose, and the like. In one embodiment, the hydroxyalkylcellulose is hydroxypropylcellulose and/or hydroxypropylmethylcellulose.

Examples of suitable hydroxypropylmethylcelluloses include those available from Dow Chemical Corporation under the tradenames, "HPMC K4M," "HPMC K15M," and "HPMC K100M." Examples of suitable hydroxypropylcelluloses include those available from Hercules, Inc. under the tradenames, "Klucel® H(CS) and "Klucel® M".

The matrix may optionally contain other conventional, pharmaceutically acceptable auxiliary ingredients, such as fillers, conventional dry binders, sweeteners, disintegrants, and lubricants such as, for example, stearic acid, magnesium stearate, and mixtures thereof.

Suitable fillers include water-disintegratable, compressible carbohydrates such as, for example, sugars, sugar alcohols, starch hydrolysates, and mixtures thereof. Examples of suitable sugars include, but are not limited to dextrose, sucrose, maltose, and lactose. Examples of suitable sugar alcohols include, but are not limited to mannitol, sorbitol, maltitol, xylitol, and erythritol. Examples of suitable starch hydrolysates include, but are not limited to, dextrins and maltodextrins.

In one embodiment, the water-disintegratable, compressible carbohydrate may be selected from dextrose monohydrate, mannitol, sorbitol, xylitol, and mixtures thereof. In embodiments in which a water-disintegratable compressible carbohydrate is employed as a filler, it is typically present at a level from, based upon the total weight of the dosage form, from about 40 to about 90 percent, e.g. from about 50 to about 80 percent.

The matrix may also incorporate pharmaceutically acceptable adjuvants, including, for example, preservatives, flavors such as, for example, orange and/or vanilla, acidulants, glidants, surfactants, and coloring agents such as, for example, FD&C yellow. However, the matrix preferably comprises no more than, based upon the total weight of the dosage form, about 25 weight % of such optional auxiliary ingredients.

The dosage form may be made in any manner, and for tablet dosage forms, a variety of tableting methods are known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art, and are described in detail in, for example, Lachman, et al., *The Theory and Practice of Industrial Pharmacy*, Chapter 11, ($3^{rd}$ Ed. 1986), which is incorporated by reference herein.

In the direct compression tableting method, a blend of the active ingredient, which may optionally be coated with a tastemasking coating, hydroxyalkylcellulose, and any other appropriate optional ingredients are directly compacted. After all ingredients are blended together, a pre-determined volume of particles from the blend is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar.

In one embodiment, the tableting method is carried out such that the resulting tablet is relatively soft. The hardness of a "soft" tablet produced in accordance with the present invention is up to about 15 kiloponds per square centimeter (kp/cm$^2$), i.e., e.g., from about 1 kp/cm$^2$ to 8 kp/cm$^2$ or from about 2 kp/cm$^2$ to 6 kp/cm$^2$. Hardness is a term used in the art to describe the diametrical breaking strength as measured by conventional pharmaceutical hardness testing equipment, such as a Schleuniger Hardness Tester. In order to compare values across differently-sized tablets, the breaking strength is normalized for the area of the break (which may be approximated as tablet diameter times thickness). This normalized value, expressed in kp/cm$^2$, is sometimes referred in the art as "tablet tensile strength." A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329, which is incorporated by reference herein.

The tablet of the present invention advantageously has acceptable friability. Friability levels are typically less than about 2%, e.g. less than about 1%, or less than about 0.5%. A discussion of tablet friability is presented in USP 23 (1995) <1216> p. 1981.

The dosage form of the present invention typically has a moisture content of not more than about 5 percent, as measured by weight loss on drying at 105° C. in a moisture analyzer, such as that available from Arizona Instruments under the tradename, "Computrac Max 2000."

We have unexpectedly found that the addition of high weight average molecular weight hydroxyalkylcellulose to the matrix results in a dosage form that delivers a good mouth-feel through a rapid viscosity build without an initial intense drying sensation of the mouth and without a subsequent excessive slimy or gummy feel during mastication. Although the increase in viscosity will depend upon several factors such as, for example, the amount and molecular weight of such hydroxyalkylcellulose used and the amount and type of active ingredient, generally the use of about 0.1 percent to about 25.0 percent of a 60,000 to about 5,000,000 MW hydroxyalkylcellulose based upon the total weight of the dosage form, will result in a viscosity increase during tablet mastication that is similar to that obtained using gums, but without the drying sensation and without the subsequent excessive slimy or gummy feel imparted by using conventional agents.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Preparation of Tastemasking Coating Solution

A coating solution was prepared by dispersing cellulose acetate, hypromellose phthalate (HPMCP-50), and polysorbate-80 in a solvent consisting of 90% acetone and 10% water under ambient conditions, so that the finished solution contained 10% of the coating materials. The relative amounts of coating materials were, based upon the total weight percent of the final coating,

| | |
|---|---|
| Cellulose acetate | 43% |
| HPMCP-50* | 53% |
| Polysorbate-80 | 4% |

*available from Shin-Etsu, Inc.

Example 2

Preparation of Coated Active Ingredient

Preparation of Ibuprofen Pre-Mixture:

Ibuprofen USP powder was combined with colloidal silicon dioxide and microcrystalline cellulose to form the following ibuprofen pre-mixture:

| Component | Weight Percent* |
|---|---|
| Colloidal silicon dioxide | 0.27% |
| microcrystalline cellulose** | 1.04% |
| Ibuprofen USP | 98.71% |

*based upon total weight of Ibuprofen pre-mixture
**available from FMC Biopolymer under the tradename, "Avicel"

Preparation of Granulation Solution:

A simethicone emulsion available from Dow Corning Company under the tradename, "30% Simethicone Emulsion USP Q7-2587" was added to an 8% solids hydroxypropylmethylcellulose aqueous solution under ambient conditions to form the following granulating solution:

| Component | Weight Percent* |
|---|---|
| Simethicone emulsion | 0.10% |
| Hydroxypropylmethylcellulose** | 7.90% |
| Water | 92.00% |

*based upon total weight of granulating solution
**available from the Dow Chemical Company under the tradename, "E 15"

Preparation of Ibuprofen Granules:

The ibuprofen mixture was then granulated to a larger particle sizes of approximately 206 μm by first spraying the granulating solution thereon at a rate of about 1200 g/min under product temperature conditions of about 19° C. using a Model GRG 600 fluid bed granulator available from Glatt, Inc. and then subsequently drying the sprayed ibuprofen at a product temperature of 23° C.

The final dried, ibuprofen granules had the following formulation

| Component | Weight Percent* |
|---|---|
| Ibuprofen | 95.7% |
| hydroxypropylmethylcellulose. | 3.01% |
| colloidal silicon dioxide | 0.25% |
| microcrystalline cellulose | 1.00% |
| simethicone emulsion | 0.04% |

The resulting ibuprofen granules were then coated with the taste-masking solution described in Example 1 at a rate of bout 375 g/min in a Wurster fluid bed coating unit under product temperature conditions of about 29° C. The resulting coated ibuprofen granules contained, based upon the total dry weight of the ibuprofen granules and the tastemasking coating, about 25% of the taste-masking coating.

Example 3

Production of Hydroxyalkylcellulose Tablet and Mouthfeel Evaluation Thereof

A batch of tablets having the formulation set forth in Table A below was made and then taste tested for mouthfeel and texture during mastication.

TABLE A

| Ingredient | Tradename | Supplier | Mg/tablet | %/batch |
|---|---|---|---|---|
| Flavor | | | 10.64 | 1.33 |
| Microcrystalline Cellulose | Avicel | | 40.00 | 5.00 |
| Mannitol | | | 417.81 | 52.23 |
| Sucralose | | McNEIL-PPC, Inc. | 2.64 | 0.33 |
| Crospovidone - NF | Polyplasdone | ISP Corp. | 8.00 | 1.00 |
| Colorant | | | 1.36 | 0.17 |
| 72% Coated Ibuprofen* | | | 278.55 | 34.82 |
| Lubricant - magnesium stearate | | | 5.00 | 0.63 |
| Acidulant - citric acid | | | 4.00 | 0.50 |
| High MW hydroxypropyl-methylcellulose | HPMC K4M | Dow Chemical Corp. | 32.00 | 4.00 |
| TOTAL | | | 800.00 | 100.0 |

*Ibuprofen particle coated with Cellulose acetate/Hydroxypropyl Methylcellulose Phthalate/Polysorbate 80 as prepared in accordance with Example 2

Preparation of Tablets:

In one container, the colorant, flavor, sucralose NF, acidulent, high molecular weight hydroxypropylmethylcellulose) and crospovidone NF were sieved through a 40 mesh screen to form an excipient blend.

The mannitol was then sieved through a 40 mesh screen and added to the blend.

The coated ibuprofen was then sieved through a 20 mesh screen and added to the blend.

The resulting blend was then manually blended in a plastic blender until the mixture was homogenous.

The lubricant was then sieved through a 40 mesh screen, added to the total resulting mixture, and manually blended until the final mixture was homogenous. The final mixture was then compressed into 800 mg chewable tablets using ½" diameter flat faced tooling to a thickness of 0.219" inches and a hardness of 5.2 kp. under ambient conditions.

This procedure was repeated, but with the omission of the high molecular weight hydroxypropylmethylcellulose ingredient.

Samples of the resulting tablets were evaluated by a laboratory panel in a blinded study for grittiness during mastication. The results of the evaluation demonstrated that the high weight average molecular weight hydroxyalkylcellulose-containing tablets had significantly less of a grittiness feel in the mouth in comparison to those tablets lacking the high weight average molecular weight hydroxyalkylcellulose.

We claim:

1. A method of administering a pharmaceutically active ingredient, said method comprising placing in the oral cavity a dosage form comprising:
   a) a plurality of particles comprising a pharmaceutically active ingredient; and
   b) a matrix comprising, based upon the total weight of the dosage form, from about 0.1 percent to about 25 percent of a hydroxyalkylcellulose having a weight average molecular weight of from about 60,000 to about 5,000,000 and/or a viscosity of from about 3,000 mPa·S to about 150,000 mPa·s in a 2% aqueous solution,
   wherein the pharmaceutically active ingredient is coated with a taste masking coating, said dosage form is a tablet having a moisture content of not more than about five percent, and said method comprises chewing said dosage form prior to swallowing said dosage form.

2. A method of claim 1, wherein the hydroxyalkylcellulose is a hydroxypropylcellulose having a weight average molecular weight of from about 140,000 to about 1,150,000.

3. A method of claim 1, wherein the hydroxyalkylcellulose is a hydroxypropylmethylcellulose having a viscosity of from about 3,000 mPa·S to about 150,000 mPa·s in a 2% aqueous solution.

4. A method of claim 1, wherein the matrix further comprises a water-disintegratable, compressible carbohydrate selected from the group consisting of dextrose monohydrate, mannitol, sorbitol, xylitol, and mixtures thereof.

5. A method of claim 1, wherein the pharmaceutically active ingredient is selected from the group consisting of acetaminophen, acetyl salicylic acid, ibuprofen, naproxen, ketoprofen, flurbiprofen, diclofenac, cyclobenzaprine, meloxicam, rofecoxib, celecoxib, pseudoephedrine, phenyl-propanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

6. A method of claim 1, wherein the dosage form is comprised of, based upon the total weight of the dosage form,
   a) from greater than about 0.25 percent and less than about 70 percent of the coated particles comprising the pharmaceutically active ingredient, said coated particles comprising, based upon the total weight of the coated particles, from greater than about 1 percent and less than about 50 percent of the taste masking coating; and
   b) from greater than about 0.5 percent and less than about 10 percent of the hydroxyalkylcellulose in the matrix.

7. A method of claim 6, wherein the taste masking coating is comprised of:
   a) at least one solubilizable polymer; and
   b) at least one insoluble film forming polymer.

8. A method of claim 7, wherein the solubilizable polymer is selected from the group consisting of enteric polymers, reverse enteric polymers, water soluble polymers, and mixtures and copolymers thereof.

9. A method of claim 8, wherein the enteric polymers are selected from the group consisting of shellac, hydroxypropyl methylcellulose phthalate, hydroxypropyl methylcellulose acetate succinate, cellulose acetate phthalate, polyvinylacetate phthalate, polymethacrylate-based polymers and mixtures and copolymers thereof.

10. A method of claim 8, wherein the enteric polymers are selected from the group consisting of hydroxypropyl methylcellulose phthalate, hydroxypropyl methylcellulose acetate succinate, cellulose acetate phthalate, polyvinylacetate phthalate, and mixtures thereof.

11. A method of claim 8, wherein the reverse enteric polymers are methylaminoethyl-methacrylate and/or neutral methacrylic acid esters.

12. A method of claim 8, wherein the water soluble polymers are selected from the group consisting of hydroxypropylmethylcellulose, hydroxypropylcellulose, hydroxyethyl-cellulose, methylcellulose, polyvinyl pyrrolidone, polyethylene glycol, polyvinyl alcohols, sodium carboxymethylcellulose, and mixtures thereof.

13. A method of claim 7, wherein the insoluble film forming polymers are selected from the group consisting of cellulose acetate, cellulose acetate butyrate, cellulose triacetate, ethylcellulose, neutral ester co-polymer of ethyl acylate and methyl methacrylate, poly(ethyl acrylate, methyl methacrylate, trimethylammonioethyl methacrylate chloride) in a ratio of 1:2:0.1, and mixtures and copolymers thereof.

14. A method of claim 1, wherein the taste masking coating is comprised of:
   a) a first polymer selected from the group consisting of cellulose acetate and/or cellulose acetate butyrate; and
   b) a second polymer selected from the group consisting of enteric polymers, reverse enteric polymers, water soluble polymers, and mixtures and copolymers thereof, wherein the weight ratio of the second polymer to the first polymer is within the range of about 5:95 to about 80:20.

15. A method of claim 7, wherein the hydroxyalkylcellulose is selected from the group consisting of hydroxymethylcellulose, hydroxyethylcellulose, hydroxypropylcellulose, hydroxyethylmethylcellulose, hydroxypropylmethylcellulose, and mixtures thereof.

16. A method of claim 7, wherein the hydroxyalkylcellulose is hydroxypropylcellulose and/or hydroxypropylmethylcellulose.

17. A method of claim 7, wherein the dosage form manufactured by a direct compression or dry granulation followed by compression.

18. A method of claim 7, wherein said dosage form meets USP dissolution requirements for immediate release forms of said pharmaceutically active ingredient.

19. A method of administering a pharmaceutically active ingredient, said method comprising placing in the oral cavity a dosage form comprising:
   a) a plurality of coated particles comprising, based upon the total weight of the dosage form, from greater than about 12 percent and less than about 40 percent of a pharmaceutically active ingredient selected from the group consisting of acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof, said coated particles further comprising, based upon the total weight of the coated particles, from greater than about 5 percent and less than about 30 percent of a taste masking coating comprised of cellulose acetate, hydroxypropyl methylcellulose phthalate, and polysorbate-80 at a ratio of 43:53:4, wherein the taste masking coating substantially covers the active ingredient; and
   b) a matrix comprising, based upon the total weight of the dosage form, from about 0.5 percent to about 10.0 percent of hydroxypropylmethylcellulose and/or hydroxypropylcellulose having a weight average molecular weight of from about 60,000 to about 5,000,000 and/or a viscosity of from about 3,000 mPa·S to about 150,000 mPa·s in a 2% aqueous solution;
   wherein said dosage form is a tablet having a moisture content of not more than about five percent, and said method comprises chewing said dosage form prior to swallowing said dosage form.

20. A method of claim 19, wherein the matrix further comprises a water-disintegratable, compressible carbohydrate selected from the group consisting of dextrose monohydrate, mannitol, sorbitol, xylitol, and mixtures thereof.

* * * * *